United States Patent [19]

Törmälä

[11] Patent Number: 4,490,612
[45] Date of Patent: Dec. 25, 1984

[54] METHOD FOR THE MEASUREMENT OF THE PROPERTIES OF A PLASTIC FILM BY MEANS OF INFRA-RED RADIATION

[75] Inventor: Sauli J. Törmälä, Espoo, Finland

[73] Assignee: Topwave Instruments Oy, Helsinki, Finland

[21] Appl. No.: 407,386

[22] Filed: Aug. 12, 1982

[30] Foreign Application Priority Data

Aug. 18, 1981 [FI] Finland .................................. 812546

[51] Int. Cl.³ .............................................. G01J 1/00
[52] U.S. Cl. .................................... 250/339; 250/341; 250/349
[58] Field of Search .............. 250/338, 339, 340, 341, 250/349, 350, 353

[56] References Cited

U.S. PATENT DOCUMENTS 3,043,956  7/1962  Cohen ................................ 250/350
3,821,550  6/1974  Priest ................................. 250/339
3,825,755  7/1974  Ruskin ............................... 250/349
4,304,995  12/1981 Huttunen et al. ................... 250/339

Primary Examiner—Janice A. Howell
Attorney, Agent, or Firm—Biebel, French & Nauman

[57] ABSTRACT

In the present publication, a method is described for the measurement of the properties, particularly of the thickness, of a plastic film (2) by transmitting infra-red radiation (1) through the film (2) to be measured, whereby part of this radiation is absorbed in the film (2) concerned. The face, form, and position of the plastic object to be measured as well as irregularities in the structure of the material cause variations of intensity in the absorption measurement that do not illustrate the quantity to be measured, e.g. thickness. The object of the present invention is to eliminate said disturbance effects. The invention is based on that the disturbances caused by refraction and scattering of the IR beam as well as by unhomogeneity of the material are compensated by separating from the radiation that has passed through the plastic film two different wave-length bands and by measuring the ratio of the intensities of the different wave-length ranges. Since the refraction factor of plastic material is practically constant within two wave-length ranges placed close to each other, refraction does not affect the ratio of intensities. The different radiations (10, 14) are passed to their respective detectors (12, 13; 16, 17) for detection. Finally, the ratio of the output signals of both detectors (12, 13 and 16, 17) is calculated, whereby the value of the desired property, e.g. thickness, at the measurement point can be established on the basis of the said ratio.

18 Claims, 4 Drawing Figures

METHOD FOR THE MEASUREMENT OF THE PROPERTIES OF A PLASTIC FILM BY MEANS OF INFRA-RED RADIATION

The present invention concerns a method in accordance with the preamble of claim 1.

When properties, particularly the thickness, of a plastic film are measured by means of a method based on the absorption of infra-red radiation, measurement errors arise out of a number of different reasons, and by now it has been difficult to eliminate such errors.

Thus, a non-perpendicular surface causes a refraction of the IR beam, which refraction follows the following formula $$\frac{n_1}{n_2} = \frac{\sin \alpha_1}{\sin \alpha_2} \quad (1)$$

wherein $n_1$ = refraction factor of air
$n_2$ = refraction factor of the plastic
$\alpha_1$ = angle between the normal of the face and the radiation in the air, and
$\alpha_2$ = angle between the normal of the face and the radiation in the plastic.

The refraction effect can be divided into four main parts:

A. Parallel refraction of the IR beam taking place in an oblique face, partly by-passing the detector, which comes out as an increase in the measurement results.
B. Scattering of the IR beam caused by a curved face, partly by-passing the detector, which comes out as an increase in the measurement results.
C. Narrowing of the IR beam caused by a curved face, all of the beam coming within the sensitive zone of the detector, which comes out as a reduction in the measurement results.
D. The lens effect of thicker or thinner portions, small as compared with the IR beam, which effect comes out as an increase or reduction in the measurement results.

An unevenness of the face visible on the microscopic level again causes reflection of radiation in the face of the plastic.

The molecular structure of the plastic material causes scattering of the radiation, because the direction of an individual beam is changed when the beam strikes against the plastic molecules.

Unhomogeneity of the plastic material causes a change in the absorption factor. Such unhomogeneity consists, e.g., of variation in the contents of additives (e.g., of titanium oxide),
density variations,
variations in the orientation degree,
variations in particle size, and
variations in crystallinity.

Also, the contents of substances absorbing radiation and present in the path of the IR beam show variation.

Ageing and contamination of components causes a shifting of the operating point of the system.

The strong absorption by the plastic material causes a low signal level and a poor signal-noise ratio in the measurement system.

IR radiation in the environment also has a disturbing effect.

The object of the present invention is to eliminate the disturbance effects listed above and to provide a more usable measurement method of an entirely novel type.

The invention is, among other things, based on the following ideas:

Disturbances caused by refraction and scattering of the IR beam as well as by unhomogeneity of the material are compensated by from the radiation that has passed through the plastic layer separating two different wave-length bands and by measuring the ratio of the intensities of the different wavelength ranges. Since the refraction factor of plastic material is practically constant within two wave-length ranges placed close to each other, refraction does not affect the ratio of the intensities.

Disturbances caused by variations in the concentration of other substances absorbing radiation and occurring in the path of the IR radiation (e.g. water vapour) are eliminated by means of careful selection of filters. Disturbing substances must not have an absorption peak within the bands of penetration of the filters.

The shifting of the operating point caused by ageing and contamination of components is compensated by means of reference measurement. In the reference measurement, the ratio of the intensities of free radiation, not passing through plastic, within different bands of penetration is measured. During the measurement proper, the ratio of the intensities of the radiation that has passed through the plastic is compared with the reference measurement.

The signal level of the indicator can be made high by selecting the bands of penetration of the filters at the absorption peak placed at about 2.4 $\mu$m, said peak being typical of plastic materials. Within this area, the intensity of IR sources is relatively high.

The signal-noise ratio is improved by using a synchronous detector, in which case the width of a frequency band of the detector element is low. Moreover, the noise of the measurement frequency is filtered off the bias voltage of the detector.

The effect of any IR radiation in the environment is eliminated by using interrupted radiation and by using a detector synchronized to the interruption frequency.

More specifically, the method in accordance with the invention is characterized in what is stated in the characterizing part of claim 1.

By means of the invention, among other things, the following advantages are achieved:

Both wave-length bands are passed to the detectors as complete, whereby the signal to be detected and coming to the detector element per unit of time is as high as possible. In the method, no long integration time of the signal to be detected is required. As compared, e.g., with a time-division system, the difference is multiple.

By means of the method, it is possible to handle a wide scale of materials absorbing at different intensities. The differences in absorption between the bands of penetration of the interference filters do not vary as extensively as the absorptions themselves do. Moreover, simultaneous measurement of both bands makes use of the entire radiation (cf. preceding paragraph).

The shifting of the operating point can be compensated by means of measurement of free radiation, i.e. by means of measurement of what is called zero-intensity ratio. The advantage provided by the measurement of the ratio of the intensities within two wave-length ranges remains available to the elimination of disturbances caused by the plastic itself.

By changing the interference filters, it is also possible to measure other properties of plastic, provided that these properties cause a peak in the absorption curve of plastic.

By resolving the so-called disturbance factor, additional information is obtained on the properties of the plastic.

Since the wave-length band of an interference filter is changed when the angle between the radiation and the filter is changed, it is in most cases possible to use the same filter in both positions.

The invention will be examined below in more detail with reference to the exemplifying embodiments in accordance with the attached drawings.

Figure 1:
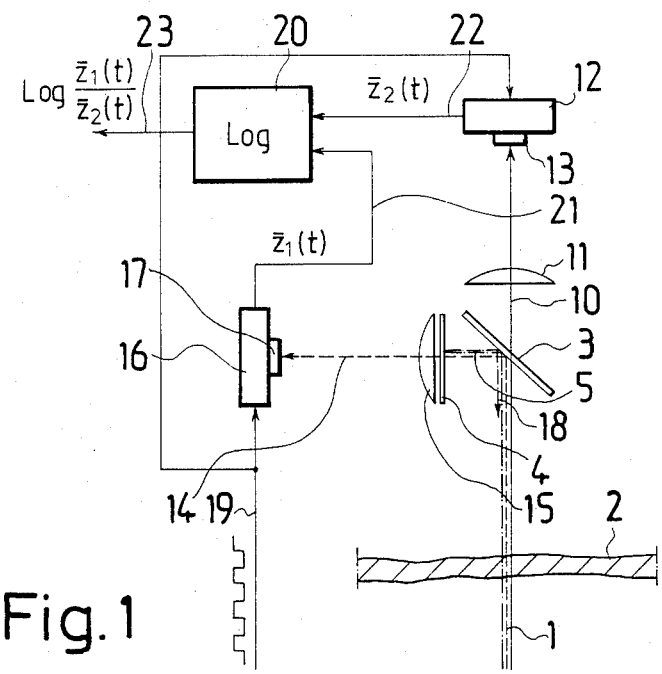
FIG. 1 is a partly schematical presentation of one measurement system by means of which the method of the invention can be applied.

According to FIG. 1, an interrupted bundle of IR beams 1 passes through the plastic film 2, and the major part of the radiation meets the interference band-pass filter 3 placed at an angle of 45° relative the direction of the radiation. The part of the radiation that does not penetrate through the filter 3 is reflected perpendicularly to the arriving radiation 1 and meets the interference band-pass filter 4. The filter 4 is mounted parallel to the arriving radiation 1, i.e., perpendicular to the reflected radiation 5.

Figure 2:
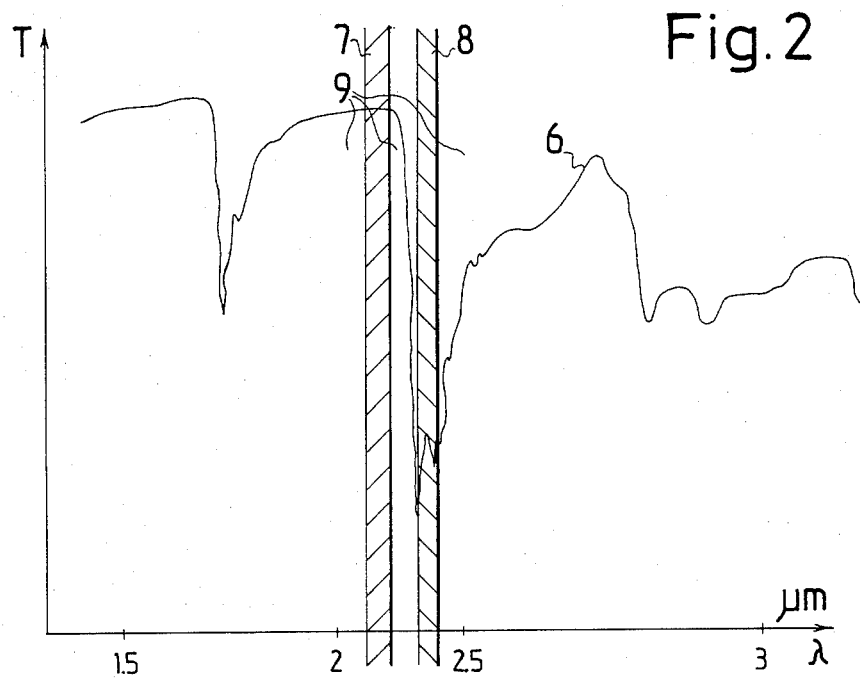
FIG. 2 shows the selection of wave-length bands on the basis of the form of the penetration curve of the plastic material.

The bands of penetration of the filters 3 and 4 have been selected, as is shown in FIG. 2, around the absorption peak 6 characteristic of the plastic material. The filter 3, as mounted at an angle of 45°, is penetrated by the wave-length range 7, and the filter 4, as mounted perpendicular to the radiation, is penetrated by the wave-length range 8. The wave-length range 9 remains outside the bands of penetration of both of the filters, so that it does not penetrate through any of the filters. Since the wave-length range 8 is placed at the absorption peak of the plastic material, the radiation placed within that range is absorbed into the material more strongly than the radiation placed within the range 7.

The part of the radiation 10 that penetrates through the filter 3 and is placed within the wave-length range 7, being focused by the lens 10, meets the photo-sensitive detector element 13 of the detector 12. The part of the radiation 14 that penetrates through the filter 4 and is placed within the wave-length range 8, being focused by the lens 15, meets the photo-sensitive detector element 17 of the detector 16. The part of the radiation 18 that does not penetrate through any of the filters 3 and 4 and that is placed within the range 9 is reflected off the detector. By diverting the filter 4 slightly from the angle of 90° relative the arriving radiation 5, it is possible to prevent the formation of a standing wave of the off-reflected radiation 18.

Since the radiation 1 is interrupted, an AC voltage is obtained from the detector elements 13 and 17, the amplitude of the said voltage being proportional to the intensity of the radiation arriving at the detector element. The detectors 12 and 16 amplify the signal coming from the elements and filter the portion of the frequency of interrupting out of the signal. In the filtering, the synchronization signal 19 of the frequency of interrupting, obtained from the interrupter, is utilized. The logarithm module 20 forms the logarithm of the ratio of the output voltages 21 and 22 of the detectors, and the output voltage 23 in this way obtained is proportional to the thickness of the plastic film 2.

The disturbance-eliminating effect of the detector construction is based on the fact that any deflection, widening or narrowing of a bundle of IR beams 1 possibly taking place in the plastic material 2 affects both of the elements 13 and 17 in the same way, whereby the ratio of the output voltages 21 and 22 of the detectors remains unchanged.

Figure 3:
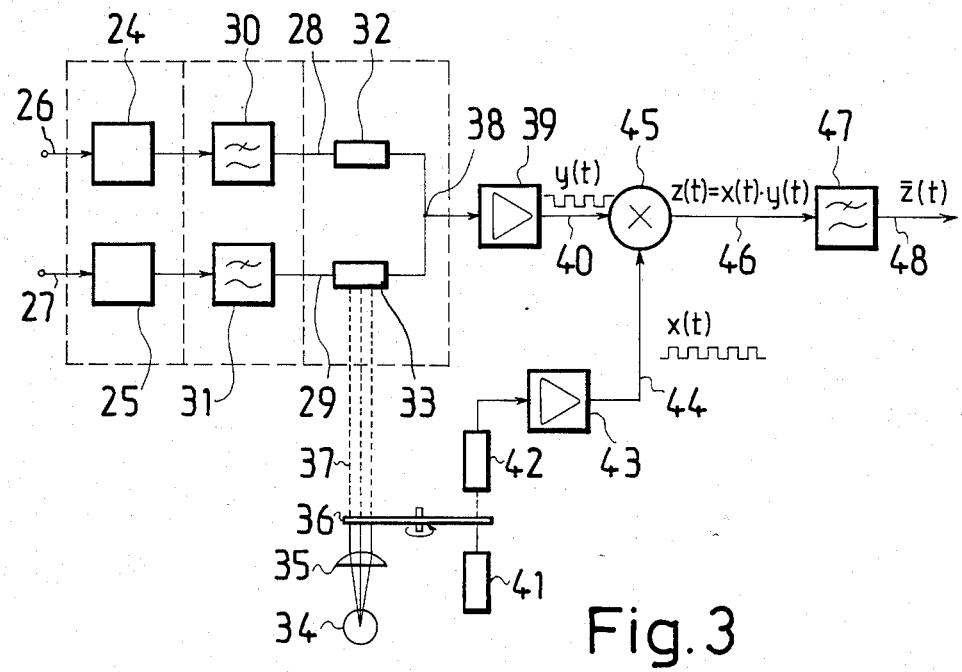
FIG. 3 is a block diagram showing a detector to be used in the system shown in FIG. 1.

The detectors 12 and 16 are identical. FIG. 3 shows a block diagram of the detectors. The regulators 24 and 25 filter the BIAS voltages 28 and 29 required by the element out of the operating voltages 26 and 27. The low-pass filters 30 and 31 limit the noise occurring in the output voltage of the regulators to a level considerably below the band of measurement. The resistance 32 functions as a load resistance of the detector element 33. The resistor 32 and the element 33 form a voltage division whose division ratio is changed in accordance with the quantity of IR radiation arriving at the detector element 33. When the radiation generated by the IR source 34, made parallel by the collimator lens 35, and interrupted by the interrupter disk 36 meets the detector element 33, an AC voltage is formed at the connection point 38 of the resistor and the element, the amplitude of the said AC voltage being proportional to the intensity of the radiation meeting the detector element.

The frequency of the voltage is the same as the frequency of the interruptions. A pre-amplifier 39 amplifies the voltage 38 to the voltage 40 of the AC component. By means of a led 41, a phototransistor, and a comparator 43, a signal 44 of the frequency of interrupting is obtained. A multiplier 45 forms the product 46 of the signals 40 and 44. The positions of the led 41 and the phototransistor 42 are adjusted so that the signal 38 to be indicated and the synchronization signal 44 are at the same phase. The low-pass filter 47 filters the signal coming from the multiplier 45 to make it an output signal 48. In accordance with the principle of operation of a synchronous detector, the voltage 46 coming from the multiplier is proportional to the portion of frequency of interrupting of the signal 38 to be indicated and to its odd harmonics. The limit frequency of the filter 47 is selected so as to be below the first odd harmonic, whereby the output voltage 48 includes only the portion of the frequency of interrupting of the signal to be indicated. The filters 30 and 31 prevent a summing of the noise of the frequency of interrupting in the signal 38 to be indicated.

The shifting of the operating point of the system caused by aging and contamination of its components is compensated for by means of a reference measurement. In the reference measurement, the ratio of the intensities of free radiation, i.e., that not passing through the plastic film, is measured within the different wavelength bands. This can be performed by operating the apparatus of FIG. 1 without the presence of the plastic film 2. During the film measurement proper, the ratio of the intensities of the radiation that has passed through the plastic is compared with the reference measurement ratio as a means of accounting for shifting of the operating point.

Within the scope of the invention, it is also possible to conceive of solutions differing from the exemplifying embodiments described above.

Thus, in stead of the first filter 3, it is possible to use a semipenetrable or partly penetrable mirror and to place the filter penetrable by the first wave-length band 7 in front of the lens 11.

The first wave-length band 7 may be selected above the absorption peak 6.

The wave-length bands of the filters 3 and 4 may be selected in the opposite sequence.

The absorption peak may also be selected from a point different from that shown in FIG. 2.

Figure 4:
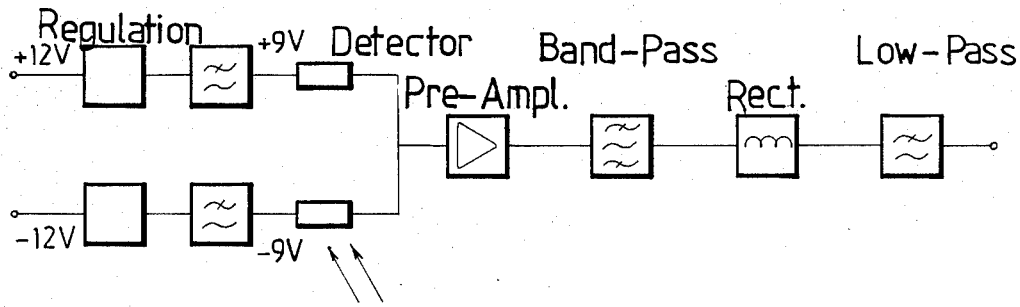
FIG. 4 is a block diagram showing an alternative detector construction.

In stead of a synchronous detector, the detector electronics may be accomplished by means of a band-pass filter and a rectifier, in accordance with FIG. 4.

The mounting angle of the first filter 3 does not have to be 45°.

The method may also be applied to reflection measurement, in which case the source of radiation and the detector are placed on the same side of the plastic film to be measured.

It is also conceivable that, in accordance with the time-division principle, two different radiations are used one after the other, in which case, e.g., two rotating filters are used.

What is claimed is:

1. Method for the measurement of the properties, particularly of the thickness, of a plastic film by transmitting at least one beam of infrared radiation through the film to be measured, whereby part of said beam is absorbed in the film concerned, comprising:

separating from the entirety of said beam that has passed through the film a first wavelength band, and separating from the entirety of said beam a second wavelength band, whose wavelength is close to said first band, said first band being placed substantially at the absorption peak of the plastic material of the film to be examined;

simultaneously passing the radiation included in said first band to a first detector for detection and passing the radiation included in said second band to a second detector for detection; and calculating the ratio of the output signals of both detectors, on the basis of which ratio it is possible to establish a value of the desired property of the plastic film to be examined at the point of measurement.

2. A method as claimed in claim 1, wherein said beam includes interrupted radiation generated by means of an interrupter and the detectors are arranged to amplify the arriving signal and filter the portion of the frequency of interruption out of the signal.

3. A method as claimed in claim 2, wherein a synchronization signal obtained from the interrupter or from the signal to be detected is utilized in the filtering.

4. A method as claimed in claim 1, wherein identical detectors are used.

5. A method as claimed in claim 1, wherein the wavelength bands are separated from the radiation that has passed through the film by means of such a first partly reflecting filter as is penetrated by the radiation included in the first band and reflects any other radiation, as well as by means of such a second partly reflecting filter to which the radiation reflected by the first filter is guided and as is penetrated by the radiation included in the second band and reflects any other radiation.

6. A method as claimed in claim 5, wherein the first filter is fitted at an angle of 45° in relation to the arriving radiation.

7. A method as claimed in claim 5, wherein the second filter is fitted at an angle slightly differing from 90° in relation to the arriving radiation or at an angle slightly differing from 45° in relation to the first filter.

8. A method as claimed in claim 5, wherein interference band-pass filters are used as the filters.

9. A method as claimed in claim 1, wherein the wavelength bands are separated from the radiation that has passed through the film by means of a semi-penetrable mirror as well as by means of two band-pass filters.

10. Method for the measurement of the properties, particularly of the thickness, of a plastic film comprising the steps of:

transmitting at least one band of infrared radiation;

separating from the entirety of said beam a first wavelength band, and separating from the entirety of said beam a second wavelength band whose wavelength is close to said first band, said first band being placed substantially at the absorption peak of the plastic material of the film to be examined;

simultaneously passing the radiation including in said first band to a first detector for detection and passing the radiation included in said second band to a second detector for detection;

calculating a reference ratio from the output signals of both detectors;

disposing the plastic film within said beam of transmitted radiation;

separating from said beam that has passed through the film said first band and said second band;

simultaneously passing the radiation included in said first band to said first detector and passing the radiation included in said second band to said second detector;

calculating a measurement ratio of the output signals of both detectors, whereupon it is possible to establish a value of a desired property of the plastic film at the point of measurement; and comparing said reference ratio with said measurement ratio for compensating for output drift of said first and second detectors.

11. A method as claimed in claim 10, wherein said beam includes interrupted radiation generated by means of an interrupter and the detectors are arranged to amplify the arriving signal and filter the portion of the frequency of interruption out of the signal.

12. A method as claimed in claim 11, wherein a synchronization signal obtained from the interrupter or from the signal to be detected is utilized in the filtering.

13. A method as defined in claim 10, wherein identical detectors are used.

14. A method as claimed in claim 10, wherein the wavelength bands are separated from the radiation that has passed through the film by means of such a first partly reflecting filter as is penetrated by the radiation included in the first band and reflects any other radiation, as well as by means of such a second partly reflecting filter to which the radiation reflected by the first filter is guided and as is penetrated by the radiation included in the second band and reflects any other radiation.

15. A method as claimed in claim 14, wherein the first filter is fitted at an angle of 45° in relation to the arriving radiation.

16. A method as claimed in claim 14, wherein the second filter is fitted at an angle slightly differing from 90° in relation to the arriving radiation or at an angle slightly different from 45° relation to the first filter.

17. A method as claimed in claim 14, wherein interference band-pass filters are used as the filters.

18. A method as claimed in claim 10, wherein the wavelength bands are separated from the radiation that has passed through the film by means of a semi-penetrable mirror as well as by means of two band-pass filters.

* * * * *